(12) United States Patent
Diaz et al.

(10) Patent No.: US 6,200,574 B1
(45) Date of Patent: *Mar. 13, 2001

(54) CHEMICAL COMPOSITION FOR AIDING THE ABSORPTION, BINDING AND ELIMINATION OF UNDIGESTED FAT

(76) Inventors: Jose A. Diaz, 2950 Jackson Ave., Coconut Grove, FL (US) 33133; Eduardo M. Naranjo, 5009 SW. 71st Pl., Miami, FL (US) 33155

( * ) Notice: Subject to any disclaimer, the term of this patent is extended or adjusted under 35 U.S.C. 154(b) by 0 days.

This patent is subject to a terminal disclaimer.

(21) Appl. No.: 09/521,224

(22) Filed: Mar. 8, 2000

Related U.S. Application Data

(63) Continuation-in-part of application No. 09/135,920, filed on Aug. 18, 1998, now Pat. No. 6,048,532, which is a continuation-in-part of application No. 08/888,848, filed on Jul. 7, 1997, now Pat. No. 5,795,576.
(60) Provisional application No. 60/021,299, filed on Jul. 8, 1996.

(51) Int. Cl.[7] .................. A61K 35/78; A61K 31/715; A61K 31/70
(52) U.S. Cl. ................ 424/195.1; 514/54; 514/62
(58) Field of Search ................ 424/195.1; 514/54, 514/62

(56) References Cited

U.S. PATENT DOCUMENTS 5,795,576 * 8/1998 Diaz et al. .................. 424/195.1

* cited by examiner

Primary Examiner—Raymond Henley, III
(74) Attorney, Agent, or Firm—Malloy & Malloy, P.A.

(57) ABSTRACT

A composition and method for reducing cholesterol, facilitating weight loss and aiding in the maintenance of a stable weight in humans, wherein the composition includes at least one preferred embodiment comprising a mixture of oat bran generally in an amount of about 83% to 85% by weight, glucosamine HCL generally in an amount about 6% to 8% by weight, glucomannan generally in an amount of 5% to 6% by weight, an amount of apple pectin or other fruit or vegetable pectin generally in an amount of about 2% by weight. Stearic acid may also be included in the composition in an amount of generally about 1% to 2% by weight of the composition.

36 Claims, No Drawings

CHEMICAL COMPOSITION FOR AIDING THE ABSORPTION, BINDING AND ELIMINATION OF UNDIGESTED FAT

CLAIM OF PRIORITY

The present application is a continuation-in-part application of application Ser. No. 09/135,920, filed on Aug. 18, 1998, now U.S. Pat. No. 6,048,532, which is a Continuation-In-Part of U.S. patent application Ser. No. 08/888,848, filed on Jul. 7, 1997, now U.S. Pat. No. 5,795,576, which was based on a claim of priority under 35 U.S.C. Section 119(e) to a provisional patent application filed with the U.S. Patent Office on Jul. 8, 1996 and assigned Ser. No. 60/021,299.

BACKGROUND OF THE INVENTION

1. Field of the Invention

The present invention relates to a chemical composition and a method for reducing cholesterol as well accomplishing weight loss in humans, whereby a human ingests the chemical composition in recommended dosages prior to eating a meal, and thereby facilitates the binding of undigested fat to a fibrous agent for rapid elimination from the human body.

2. Description of the Related Art

In this day and age, many people's lifestyles have become less physically active. A natural result of a sedentary lifestyle is the tendency to gain weight. Indeed, it is commonly thought that many people are now over-weight with obesity being a growing problem. Due to this trend, countless efforts have been made to help people control their weight. As a few examples, many have proclaimed to have won the "battle of the bulge" with a specific diet program or a particular exercise program. Others have explored hypnosis and other mechanisms for controlling the appetite of an individual. Still others in the scientific arena have formulated sugar substitutes and are pursuing fat substitutes as methods to reduce the caloric intake of an individual hopefully, without sacrificing the taste of otherwise highly fattening foods. While these efforts are generally capable of aiding many in their fight to lose weight or to maintain a desired weight, many are in general, ineffective or simply not practical. For example, some good meaning souls have tried in earnest to follow a particular diet plan but eventually, fall off the plan lacking will-power to continue for weeks and months at a time. This is equally true of those who try hypnosis and similar weight-loss gimmicks. Finally, some view sugar substitutes as being tasteless or worse, as carrying an intolerable health risk, given that some studies have linked them to carcinogens and/or the formation of brain tumors.

It has been appreciated in recent years that the fat content of foods eaten are a major culprit behind human weight gain. For example, regardless of the type of fat present in a food product, fat has the highest caloric value per gram —about 9 calories per gram—of any food group. It is understood that the body tends to store fat for future use, rather than to utilize it immediately, and this factor helps lead to weight-gain. However, in recent years it has been recognized, that there is a connection between the amount of fat stored in the body and the level of cholesterol in the body. A diet high in fat is more likely to result in the development of higher cholesterol levels. As cholesterol has been indicated as a factor in arteriosclerosis or hardening of the arteries, the risk for heart disease and/or a heart attack is elevated when a diet high in fat is followed. Unfortunately, fat also makes many food items more tasty—whether butter on bread, dressings on salads, sour cream on potatoes, or frosting on cake—and are therefore, difficult to eliminate entirely from one's diet.

Thus, fat usually finds its way into the body. Once it does so, a healthy body automatically secretes lipase, an enzyme that accelerates synthesis of fats, i.e., breaking down the fat molecule. The majority of all fats in foods are present in "triglyceride form", which the body seeks to break down by removing the glycerol molecule from the triglyceride and thereby, release the free fatty acids. Once this occurs, the body is well on its way to absorbing the fat and likely, storing same instead of utilizing it for energy.

From the foregoing, it will be understood that there remains an appreciable need in the art for a product which facilitates a person's efforts to lose weight and/or to control his or her weight and yet which is safe and easy to implement. There remains a need in the art for a product and method which aids a person in losing weight or in maintaining a stable weight, which does not rely exclusively on will power. Any such product or method should not interfere with the taste of foods. Ideally, any such product or method would permit a person to eat the foods that they most like, without being as mindful of fats contained therein. Preferably, such product or method would prevent the body from absorbing the fat in such foods once they have been eaten and further, would aid the body in rapid elimination of the absorbed fats in a safe and comfortable manner. In turn, the rapid elimination of fats subsequent to ingestion and prior to digestion, would have a highly beneficial effect in preventing the build-up or accumulation of harmful cholesterol. The present invention is designed to satisfy the needs in the art and is believed to represent a significant advance in improving a person's health by reducing harmful cholesterol and concurrently facilitating weight loss by means of the rapid elimination of the fat from the human body.

SUMMARY OF THE INVENTION

The present invention provides a novel, chemical composition for ingestion by humans which aids in reducing cholesterol, facilitates weight loss and fosters the maintenance of a stable weight. In particular, when the chemical composition of the present invention is ingested by a human prior to eating a meal, the composition acts to absorb and bind undigested fat to a fibrous agent so as to promote its rapid elimination from the human body. In accordance with this invention, the novel composition is moisture activated such that it remains inert and can be formed into capsules, preferably conveniently sized for ingestion by a human, and will remain inert until it comes into contact with water, bodily fluids or other liquids. The composition comprises a mixture of oat bran generally in an amount of about 83% to 85% by weight, glucosamine HCL generally in an amount of about 6% to 8% by weight, glucomannan generally in an amount of about 5% to 6% by weight, an amount of apple pectin or other fruit or vegetable pectin generally in an amount of about 2% by weight and stearic acid generally in an amount of about 1% to 2% by weight of the composition. Upon contact with moisture, the composition begins to break down and becomes activated. Once activated, the composition acts quickly, usually within 30 seconds to seek and attach itself to undigested fats such as oils and the like, and typically, within about 2 minutes will form a small mass of undigestible fibrous material. Additionally, a method for using the chemical composition is also described, which comprises the steps of forming a capsule of generally about 500 to 700 milligrams containing the chemical composition and having a human ingest at least one to four of these capsules with generally about eight ounces of water generally about fifteen to about twenty minutes before a meal.

A primary object of the present invention is to provide a chemical composition and method of treatment which serve as a convenient and effective means for reducing the quantity of fat digested and/or absorbed by the human body, thereby aiding in a significant reduction of harmful cholesterol levels in the body as well as a reduction of cholesterol build-up or deposits in the cardiovascular system.

Another primary object of the present invention is to provide a chemical composition which seeks out, attaches and binds undigested fat ingested by a human to a fibrous agent, forming an undigestible mass which can easily and rapidly be eliminated from the human's body.

A feature of the chemical composition according to the present invention is that it is moisture activated and therefore, is inert and can be formed into and stored as conveniently sized capsules until being ingested by a human and activated by coming into contact with bodily secretions whether water or other liquid.

Yet another object of the present invention is to provide a chemical composition which includes a blend of fibrous material for aiding the human body in rapid elimination of waste.

A feature of the present invention, in the form of one 500 milligram capsule, is that it can absorb up to twelve times its own weight or generally about 3 to 6 grams of undigested fats.

These and other objects, features and advantages of the present invention will become readily apparent from the detailed description, which follows.

DETAILED DESCRIPTION OF THE PREFERRED EMBODIMENT

The present invention is directed towards a chemical composition for ingestion by humans which acts to absorb and bind undigested fat and rapidly eliminate the undigested fat from the human body. The present invention is also directed to a method of aiding weight loss in humans. As a result of substantially reducing fat absorption by the human body, the present invention is also directed to a composition and method of significantly reducing the production of cardiovascular build-up of harmful cholesterol in humans.

The chemical composition of the present invention primarily comprises at least one fibrous agent to act both as a vehicle for absorbing fat and as a medium for allowing a human to feel full. In the preferred embodiment, the fibrous agent used is oat bran and comprises generally between 80% and 90% by weight of the composition. In one embodiment of the composition of the present invention, oat bran comprises generally about 85% by weight and in another embodiment, oat bran comprises ideally, 83% by weight of the composition. In the preferred embodiment, the composition of the present invention may additionally comprise one or more other fibrous agents. For example, plantago ovata seed mucilage or the cover or husks of natural oat bran seeds may be utilized, which are very fibrous materials. Other fibrous agents may also be utilized, as described more fully below.

In addition to a fibrous agent, the composition of the present invention comprises glucosamine, a material derived from deacetylated shellfish shells or chitin. Chitin is known in the art as a naturally occurring polysaccharide—a polymer of long molecules consisting of sugar molecules strung together as shown by the general formula:

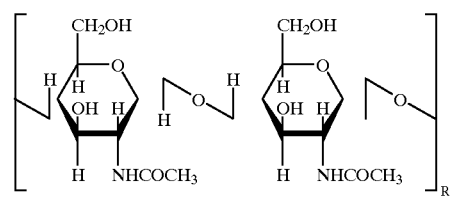

Chitin, which can be obtained from crab, lobster or shrimp shells by dissolving the shells' with calcium carbonate and then removing protein fragments, leaving behind chitin as a white powder, normally cycles through the environment, decomposing naturally into its hydrogen, carbon, nitrogen and oxygen building blocks. In one embodiment of the invention, glucosamine may be obtained from chitin by hydrolysis. Preferably, glucosamine salts and compounds derived from a monomer of chitin, namely, N-acetyl-D-glucosamine (GlcN Ac) which is represented by the general formula:

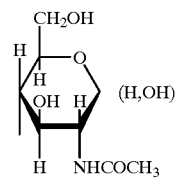

will be utilized such as, for example, glucosamine hydrochloride, acetylated glucosamine, and/or D-glucosamine. In a most preferred embodiment, glucosamine HCL and/or glucosamine hydrochloride will be utilized and will comprise generally about 10% and ideally 8% by weight of the composition. In another embodiment, glucosamine HCL or glucosamine hydrochloride will comprise generally about 6% to 7% by weight, and ideally, 6% by weight of the composition. Glucosamine hydrochloride offers an additional side benefit in that it has been shown to be an efficacious alternative to corticosteroid treatment of enteritis and colitis. It will be understood by those of ordinary skill in the art that as a derivative of chitosan, which has an ability to chelate various metal ions because its hydroxy and amino groups act as electron donors, glucosamine HCL is an ion, or molecule having a negative charge, and which therefore, attracts and binds with certain molecules of food. In an alternative embodiment, a beta-alkylglycoside of N-acetyl-D-glucosamine may be utilized, which is represented by the general formula:

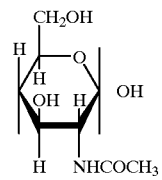

and is believed to effectively increase the ability of one's digestive tract to handle substantial quantities of lactose. In yet another alternative embodiment, the composition may comprise chitosan, instead of glucosamine. Chitosan is formed by subjecting the chitin, in white powder form, to a concentrated sodium hydroxide solution heated to above 135 degrees Celsius to remove one of chitin's side groups, i.e., to hydrolize the N-acetyl linkage, which results in chitosan, which can be more readily dissolved. Chitosan, which is represented by the general formula:

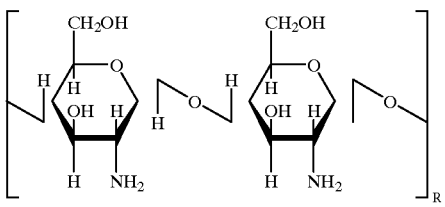

also has the ability to act as a coagulant, i.e., to attract and bind with certain molecules, such as amino acids and proteins.

In the preferred embodiment of the present invention, the chemical composition comprises, in addition to oat bran and glucosamine HCL, a quantity of glucomannan—also known as Konjak or Konjac Root—which serves the purpose of providing lubrication and as well as providing an additional fibrous agent to the composition. In one embodiment of the composition of the present invention glucomannan comprises generally about 5% to 6% by weight and ideally 6% by weight of the composition. In addition, the chemical composition further comprises a pectin obtained from fruits or vegetables which serves the purpose of providing an additional fibrous agent to the composition. Most preferably, an apple pectin is used to form the composition which ideally, comprises generally about 2% by weight of the composition. Finally, in at least one embodiment, the chemical composition also comprises a saturated fatty acid, such as stearic acid, which serves the purpose of permitting the capsule containing the composition to be smooth. Ideally, stearic acid comprises generally about 1% to 2% by weight of the composition.

In one preferred embodiment, the oat bran, glucosamine HCL, glucomannan, apple pectin and stearic acid are mixed together in powder form, although a granular form might also be suitable, and result in a mixture which is inert until it comes into contact with water, or another liquid, such as is produced by the human body during digestion. Thus, in a most preferred embodiment, the present invention can be formed into capsules so as to facilitate packaging, storage and ingestion. Additionally, the material used to form the encasement of the capsule will be inert and upon coming into contact with water or other liquid, will begin to break down and permit both the release and activation of the chemical composition. If desired, the capsules containing the chemical composition according to the present invention may be packaged into bottles containing 50, 60, 75, 80, 100 or more capsules, and may include a small, separately wrapped quantity of a drying agent, such as a silica gel in order to aid dry conditions for preserving the composition inert until use by a human.

In one embodiment, the present invention will be formed into capsules containing generally about 500 milligrams of the chemical composition in the following amounts: generally about 83% by weight of oat bran; generally about 8% by weight of glucosamine HCL; generally about 6% by weight of glucomannan; generally about 2% by weight of apple pectin; and generally about 1% by weight of stearic acid. It will be appreciated that a capsule containing about 500 milligrams has a size and overall dimension which is readily suited for being comfortably swallowed by a person, although the capsule could be formed to be contain less or more of the chemical composition (with ratios of the ingredients of the composition similar to that disclosed herein), and thereby be somewhat larger or smaller, and still function in the intended manner when ingested by a person. Testing experiments with the above described chemical composition have demonstrated the ability to absorb up to 12 times its own weight or about 3 to 6 grams of undigested fats. For instance, in one experiment 70 milliliters of water was placed in an appropriately sized test tube along with 2 grams of wheat germ oil and 100 milligrams of lecithin. This mixture was shaken vigorously for about 10 seconds. Next, 1000 milligrams of the chemical composition according to the present invention (two capsules of 500 mg each) were added and again, the mixture was shaken vigorously for about 10 seconds. After several minutes, the mixture was observed as having approximately ninety-five (95%) percent of fat (oil layer) gone, i.e., fat was no longer visible but instead had become bound with the fibrous agent of the composition so as to form an undigestible mass.

In addition, the chemical composition of the present invention lends itself to a method of aiding human weight loss, which will now be described. In particular, the chemical composition of the present invention seeks out and binds with fat ingested by a human prior to its being absorbed into the body, and as has been explained, binds them to a fibrous agent so as to aid the person in feeling "full" and further, to permit rapid elimination by the human body. The method of the present invention comprises the steps of forming a capsule of generally about 500 milligrams with the chemical composition and having the human ingest at least one of the 500 milligram capsules with generally about eight ounces of water generally about fifteen to twenty minutes before a meal. Ideally, the human will ingest one or two of the capsules before a meal, but may ingest up to about four of the capsules (2000 milligrams) if the meal to be eaten is especially large and/or has a particularly high fat content. Upon being ingested by a human, each capsule begins to disintegrate and releases or otherwise facilitates activation of the chemical composition contained therein typically, in about thirty (30) minutes, and often less time. In a preferred form of the method there is an additional step of having the human ingest generally about eight ounces of water upon waking up in the morning, and ideally, there is an additional step of having the human ingest generally about eight ounces of water between meals.

Another preferred embodiment of the chemical composition of the present invention comprises the capsules containing generally about 700 milligrams (700 mgs) of the composition in the following amounts; generally about 85% by weight of oat grand; generally about 6% by weight of glucosamine HCL; generally about 6% by weight of glucomannan; generally about 2% by weight of apple pectin; and generally about 1% by weight of stearic acid. In this embodiment of the present invention the capsule could be formed to contain less or more of the chemical composition (with ratios of the ingredients of the composition being similar to that disclosed herein), and thereby be somewhat larger or smaller and still be adequate for ingestion by a person.

In addition to a reduction in cholesterol, this latter embodiment of the chemical composition of the present invention also lends itself to a method of aiding human weight loss by seeking out and binding with a fat ingested by a human prior to the fat being absorbed by the body. As has been explained, the fat binds to the fibrous agents of the composition so as to aid the person in feeling (full) and further permits the rapid and natural elimination thereof from the human body. One preferred method utilizing this latter embodiment of the present invention comprises the steps of forming a capsule of generally about 700 milligrams with the chemical composition and having the human ingest at least 4 of the 700 milligrams capsules with generally about 8 ounces of water, approximately 15 to 20 minutes before a meal is to be consumed. Thus the intake of oat bran with each capsule is generally about 600 milligrams or multiplying by 4, 24 hundred milligrams per meal, and if three meals per day are consumed, the intake would then be 7200 milligrams of oat bran per day. This amount of oat bran being consumed, has been shown to significantly aid in the reduction of cholesterol. From the foregoing, it should be clear that a human may ingest more than 4 of such capsules and even up to 6 or more of such capsules, if the meal to be eaten is especially large and/or has a particularly high fat content. Upon being ingested, each capsule begins to disintegrate and releases the chemical composition contained therein, in generally about 30 minutes and often less time. In one preferred form of the method of the present invention utilizing this latter embodiment, there is an additional step of having the human ingest generally about 8 ounces of water upon waking in the morning and ideally, there is an additional step of having the human ingest about 8 ounces of water between meals.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described,

What is claimed is:

1. A chemical composition for ingestion by a human at meal-times, which aids in absorbing and binding undigested fat for rapid elimination from the human's body, said composition comprising:
    a) a predetermined amount of oat bran;
    b) a predetermined amount of glucosamine HCL;
    c) a predetermined amount of glucomannan; and
    d) a predetermined amount of fruit or vegetable pectin.

2. A chemical composition as recited in claim 1 further comprising a predetermined amount of stearic acid.

3. The chemical composition as recited in claim 1 further comprising said oat bran present in an amount of generally about 83% by weight of said compositions; said glucosamine HCL present in an amount of generally about 8% by weight; said glucomannan present in an amount generally about 6% by weight and said fruit or vegetable pectin present in an amount generally about 2% by weight.

4. A chemical composition as recited in claim 3 further comprising stearic acid present in an amount generally about 1% by weight.

5. A chemical composition as recited in claim 3 wherein said fruit or vegetable pectin comprises apple pectin.

6. A chemical composition as recited in claim 1, wherein said composition is formed into a capsule of between 500 and 700 milligrams.

7. A chemical composition as recited in claim 1, wherein said composition is formed into a capsule of about 500 milligrams.

8. A method of absorbing and binding undigested fat ingested by a human and for rapidly eliminating same from the human, said method comprising the steps of:
    a) forming a capsule of generally about 500 to 700 milligrams with the chemical composition as recited in claim 1, and
    b) having the human ingest at least one of said capsules with generally about eight ounces of water generally about fifteen minutes before a meal.

9. A method of absorbing and binding undigested fat ingested by a human and for rapidly eliminating same from the human, said method comprising the steps of:
    a) forming a capsule of generally about 500 milligrams with a chemical composition comprising;
        i) an amount of oat bran generally about 83% by weight of said composition;
        ii) an amount of glucosamine HCL generally about 8% by weight of said composition;
        iii) an amount of glucomannan generally about 6% by weight of said composition; and
        iv) an amount of apple pectin generally about 2% by weight of said composition;
    b) having the human ingest at least one of said capsules with generally about eight ounces of water generally about fifteen minutes before a meal.

10. A method as recited in claim 9 wherein the composition further comprises an amount of stearic acid generally about 1% by weight.

11. A method as recited in claim 9, wherein the human ingests two of said capsules.

12. A method as recited in claim 9, wherein the human ingests three of said capsules.

13. A method as recited in claim 9, wherein the human ingests four of said capsules.

14. A method as recited in claim 9, further comprising the step of having the human ingest generally about eight ounces of water upon waking up in the morning.

15. A method as recited in claim 9, further comprising the step of having the human ingest generally about eight ounces of water between meals.

16. A chemical composition designed for the reduction of cholesterol in the human body, said composition comprising:
    a) a predetermined amount of oat bran;
    b) a predetermined amount of glucosamine HCL;
    c) a predetermined amount of glucomannan; and
    d) a predetermined amount of fruit or vegetable derived pectin.

17. A chemical composition as recited in claim 16 wherein said oat bran is present in quantities generally between 84% and 85% by weight; said glucosamine HCL is present in quantities generally between 6% and 7% by weight; said glucomannan is present in quantities generally between 5% and 6% by weight; and said fruit or vegetable derived pectin is present in quantities generally about 2% by weight.

18. A chemical composition as recited in claim 17 wherein said fruit or vegetable derived pectin is apple pectin.

19. A chemical composition as recited in claim 18 further comprising an amount of stearic acid generally between 1% and 2% by weight of said composition.

20. A chemical composition as recited in claim 17 further comprising an amount of stearic acid generally between 1% and 2% by weight of said composition.

21. A chemical composition as recited in claim 17 comprising a single dose of said composition defined by substantially seven hundred milligrams of said composition.

22. A chemical composition as recited in claim 21 wherein the single dose comprises a capsule.

23. A chemical composition for reducing cholesterol in the human body resulting from the ingestion of fatty foods, said composition comprising:
    a) an amount of oat bran generally about 85% by weight of said composition,
    b) an amount of glucosamine generally about 6% by weight of said composition, c) an amount of glucomannan generally about 6% by weight of said composition, and d) an amount of fruit or vegetable derived pectin generally about 2% by weight of said composition.

24. A chemical composition as recited in claim 23 wherein said fruit or vegetable derived pectin is apple pectin.

25. A chemical composition as recited in claim 24 further comprises an amount of stearic acid generally about 1% by weight of said composition.

26. A chemical composition for reducing cholesterol in the human body resulting from the ingestion of fatty foods, said composition comprising:

a) an amount of oat bran in quantities generally between 84% and 85% by weight of said composition.

b) an amount of chitosan generally between 6% and 7% by weight of said composition, c) an amount of glucomannan generally between 5% and 6% by weight of said composition, and d) an amount of apple pectin generally about 2% by weight of said composition.

27. A chemical composition as recited in claim 26 further comprising an amount of stearic acid generally between 1% and 2% by weight of said composition.

28. A method of reducing cholesterol in the human body, said method comprising the steps of:

a) forming a single dose having a predetermined quantity of a chemical composition comprising:
  i) an amount of oat bran in quantities generally between 84% and 85% by weight of said composition,
  ii) an amount of glucosamine HCL generally between 6% and 7% by weight of said composition,
  iii) an amount of glucomannan generally between 5% and 6% by weight of said composition,
  iv) an amount of apple pectin generally about 2% by weight of said composition, and b) having a human ingest at least one of said single doses prior to a meal.

29. A method as recited in claim 28 comprising forming the single dose by further including an amount of stearic acid generally between 1% and 2% by weight of said composition.

30. A method as recited in claim 29 comprising having the human ingest an amount of at least substantially 2800 milligrams of said composition prior to each meal.

31. A method as in claim 28 comprising defining the single dose to be an amount of substantially about 700 milligrams.

32. A method as in claim 31 comprising having a human ingest at least four doses of said composition before each meal.

33. A method as in claim 28 wherein said single dose is in capsule form.

34. A method of reducing cholesterol in the human body, said method comprising the steps of:

a) forming a single dose having a predetermined quantity of a chemical composition comprising:
  i) an amount of oat bran in quantities in generally about 85% by weight of said composition,
  ii) an amount of chitosan generally about 6% by weight of said composition,
  iii) an amount of glucomannan generally about 6% by weight of said composition,
  iv) an amount of apple pectin generally about 2% by weight of said composition, b) having a human ingest at one of said single doses prior to a meal.

35. A method as recited in claim 34 comprising having the human ingest an amount of at least 2800 milligrams of said composition prior to each meal.

36. A method as recited in claim 34 further comprising forming the single dose of said chemical composition into a capsule of substantially about 700 milligrams.

\* \* \* \* \*